(12) United States Patent
Fitzgerald et al.

(10) Patent No.: US 8,545,414 B2
(45) Date of Patent: Oct. 1, 2013

(54) METHODS AND DEVICES FOR MODULATION OF HEART VALVE FUNCTION

(75) Inventors: Peter J. Fitzgerald, Portola Valley, CA (US); Ali Hassan, Mountain View, CA (US); Brian K. Courtney, Ontario (CA); Nicolas A. F. Chronos, Atlanta, GA (US); Richard G. Cartledge, Fort Lauderdale, FL (US); Leonard Y. Lee, New York, NY (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 809 days.

(21) Appl. No.: 11/587,765

(22) PCT Filed: Apr. 29, 2005

(86) PCT No.: PCT/US2005/015323
§ 371 (c)(1),
(2), (4) Date: Dec. 12, 2008

(87) PCT Pub. No.: WO2005/107862
PCT Pub. Date: Nov. 17, 2005

(65) Prior Publication Data
US 2009/0234404 A1     Sep. 17, 2009

Related U.S. Application Data

(60) Provisional application No. 60/567,320, filed on Apr. 30, 2004.

(51) Int. Cl.
*A61B 5/02*          (2006.01)

(52) U.S. Cl.
USPC .......... 600/526; 600/374; 607/119; 607/122; 607/123; 607/62; 607/6; 607/9; 607/11; 607/17

(58) Field of Classification Search
USPC ............... 607/119, 122, 123, 62, 6, 9, 11, 17; 600/526, 374
See application file for complete search history.

(56) References Cited

U.S. PATENT DOCUMENTS

| 4,676,253 A | 6/1987 | Newman et al. |
| 5,119,674 A | 6/1992 | Nielsen |

(Continued)

FOREIGN PATENT DOCUMENTS

| EP | 0620420 A1 | 10/1994 |
| JP | 09-066114 | 3/1997 |
| WO | 96/25978 A1 | 8/1996 |

OTHER PUBLICATIONS

International Search Report dated Sep. 21, 2005 for International Application No. PCT/US2005/015323.

(Continued)

*Primary Examiner* — Christopher D Koharski
*Assistant Examiner* — Natasha Patel
(74) *Attorney, Agent, or Firm* — Lerner, David, Littenberg, Krumholz & Mentlik, LLP

(57) ABSTRACT

Methods and devices for modulating heart valve function are provided. In the subject methods, a heart valve is first in structurally modified. Blood flow through the structurally modified heart valve is then monitored, and the heart is paced in response to the monitored blood flow. Also provided are devices, systems and kits that find use in practicing the subject methods. The subject methods find use in a variety of applications.

55 Claims, 6 Drawing Sheets

(56) References Cited

U.S. PATENT DOCUMENTS

| | | | |
|---|---|---|---|
| 5,139,020 A | 8/1992 | Koestner et al. | |
| 5,243,976 A * | 9/1993 | Ferek-Petric et al. | 607/6 |
| 5,318,595 A | 6/1994 | Ferek-Petric et al. | |
| 5,354,330 A | 10/1994 | Hanson et al. | |
| 5,487,760 A * | 1/1996 | Villafana | 623/2.2 |
| 6,398,734 B1 * | 6/2002 | Cimochowski et al. | 600/454 |
| 6,402,781 B1 | 6/2002 | Langburg et al. | |
| 6,868,739 B1 * | 3/2005 | Krivitski et al. | 73/861.05 |
| 7,175,660 B2 | 2/2007 | Cartledge et al. | |
| 7,297,150 B2 | 11/2007 | Cartledge et al. | |
| 7,455,690 B2 | 11/2008 | Cartledge et al. | |
| 7,643,879 B2 * | 1/2010 | Shuros et al. | 607/18 |
| 8,005,544 B2 * | 8/2011 | Zhu et al. | 607/9 |
| 2003/0078465 A1 * | 4/2003 | Pai et al. | 600/16 |
| 2006/0106405 A1 | 5/2006 | Fann et al. | |
| 2006/0241748 A1 | 10/2006 | Lee et al. | |
| 2007/0016287 A1 | 1/2007 | Cartledge et al. | |
| 2007/0299543 A1 | 12/2007 | Cartledge et al. | |
| 2008/0027483 A1 | 1/2008 | Cartledge et al. | |
| 2008/0109076 A1 | 5/2008 | Cartledge et al. | |
| 2008/0306586 A1 | 12/2008 | Cartledge et al. | |
| 2009/0125102 A1 | 5/2009 | Cartledge et al. | |
| 2010/0305609 A1 | 12/2010 | Cartledge et al. | |
| 2011/0009956 A1 | 1/2011 | Cartledge et al. | |
| 2011/0022168 A1 | 1/2011 | Cartledge | |
| 2011/0066231 A1 | 3/2011 | Cartledge et al. | |
| 2011/0093062 A1 | 4/2011 | Cartledge et al. | |
| 2011/0196480 A1 | 8/2011 | Cartledge | |
| 2011/0202130 A1 | 8/2011 | Cartledge et al. | |
| 2011/0208295 A1 | 8/2011 | Cartledge et al. | |
| 2011/0257633 A1 | 10/2011 | Cartledge et al. | |

OTHER PUBLICATIONS

U.S. Appl. No. 13/123,768.
Letter dated Jan. 27, 2011 from Richard H. Levinstein, Esq.
U.S. Appl. No. 13/123,768, filed Apr. 2, 2011.

* cited by examiner

METHODS AND DEVICES FOR MODULATION OF HEART VALVE FUNCTION

CROSS-REFERENCE TO RELATED APPLICATIONS

Pursuant to 35 U.S.C. §119 (e), this application claims priority to the filing date of the U.S. Provisional Patent Application Ser. No. 60/567,320 filed Apr. 30, 2004; the disclosure of which is herein incorporated by reference.

INTRODUCTION

Background of the Invention

Congestive heart failure (CHF), which is often associated with an enlargement of the heart, is a leading cause of death. As a result, the market for the treatment of CHF is becoming increasingly prevalent. For instance, the treatment of CHF is a leading expenditure of Medicare and Medicaid dollars in the United States of America. Typically, the treatment of CHF enables many who suffer from CHF to enjoy an improved quality of life.

Referring initially to FIG. 1, the anatomy of a heart, specifically the left side of a heart, will be described. The left side of a heart 104 includes a left atrium 108 and a left ventricle 112. An aorta 114 receives blood from left ventricle 112 through an aortic valve 120, which serves to prevent regurgitation of blood back into left ventricle 112. A mitral valve 116 is disposed between left atrium 108 and left ventricle 112, and effectively controls the flow of blood between left atrium 108 and left ventricle 112.

Mitral valve 116, which will be described below in more detail with respect to FIG. 2a, includes an anterior leaflet and a posterior leaflet that are coupled to cordae tendonae 124 which serve as "tension members" that prevent the leaflets of mitral valve 116 from opening indiscriminately. When left ventricle 112 contracts, cordae tendonae 124 allow the anterior leaflet to open upwards until limited in motion by cordae tendonae 124. Normally, the upward limit of opening corresponds to a meeting of the anterior and posterior leaflets and the prevention of backflow. Cordae tendonae 124 arise from a columnae camae 128 or, more specifically, a musculi papillares of columnae camae 128.

Left ventricle 112 includes trabeculae 132 which are fibrous cords of connective tissue that are attached to wall 134 of left ventricle 112. Trabeculae 132 are also attached to an interventricular septum 136 which separates left ventricle 112 from a right ventricle (not shown) of heart 104. Trabeculae 132 are generally located in left ventricle 112 below columnae camae 128.

FIG. 2a is a cut-away top-view representation of mitral valve 116 and aortic valve 120. Aortic valve 120 has a valve wall 204 that is surrounded by a skeleton 208a of fibrous material. Skeleton 208a may generally be considered to be a fibrous structure that effectively forms a ring around aortic valve 120. A fibrous ring 208b, which is substantially the same type of structure as skeleton 208a, extends around mitral valve 116. Mitral valve 116 includes an anterior leaflet 212 and a posterior leaflet 216, as discussed above. Anterior leaflet 212 and posterior leaflet 216 are generally thin, flexible membranes. When mitral valve 116 is closed (as shown in FIG. 2a), anterior leaflet 212 and posterior leaflet 216 are generally aligned and contact one another to create a seal. Alternatively, when mitral valve 116 is opened, blood may flow through an opening created between anterior leaflet 212 and posterior leaflet 216.

Many problems relating to mitral valve 116 may occur and these insufficiencies may cause many types of ailments. Such problems include, but are not limited to, mitral regurgitation. Mitral regurgitation, or leakage, is the backflow of blood from left ventricle 112 into the left atrium 108 due to an imperfect closure of mitral valve 116. That is, leakage often occurs when a gap is created between anterior leaflet 212 and posterior leaflet 216.

In general, a relatively significant gap may exist between anterior leaflet 212 and posterior leaflet 216 (as shown in FIG. 2b) for a variety of different reasons. For example, a gap may exist due to congenital malformations, because of ischemic disease, or because a heart has been damaged by a previous heart attack. A gap may also be created when congestive heart failure, e.g., cardiomyopathy, or some other type of distress causes a heart to be enlarged. When a heart is enlarged, the walls of the heart, e.g., wall 134 of a left ventricle, may stretch or dilate, causing posterior leaflet 216 to stretch. It should be appreciated that anterior leaflet 212 generally does not stretch. As shown in FIG. 2b, a gap 220 between anterior leaflet 212 and stretched posterior leaflet 216' is created when wall 134' stretches. Hence, due to the existence of gap 220, mitral valve 116 is unable to close properly, and may begin to leak.

Leakage through mitral valve 116 generally causes a heart to operate less efficiently, as the heart must work harder to maintain a proper amount of blood flow therethrough. Leakage through mitral valve 116, or general mitral insufficiency, is often considered to be a precursor to CHF. There are generally different levels of symptoms associated with heart failure. Such levels are classified by the New York Heart Association (NYHA) functional classification system. The levels range from a Class 1 level which is associated with an asymptomatic patient who has substantially no physical limitations to a Class 4 level which is associated with a patient who is unable to carry out any physical activity without discomfort, and has symptoms of cardiac insufficiency even at rest. In general, correcting for mitral valve leakage may be successful in allowing the NYHA classification grade of a patient to be reduced. For instance, a patient with a Class 4 classification may have his classification reduced to Class 3 and, hence, be relatively comfortable at rest.

A variety of treatments used to correct for mitral valve leakage or, more generally, CHF, have been developed. In certain instances, the implantation of replacement valves is employed to treat mitral valve related conditions. Valves from animals, e.g., pigs, may be used to replace a mitral valve 116 in a human. While the use of a pig valve may relatively successfully replace a mitral valve, such valves generally wear out, thereby requiring additional open surgery at a later date. Mechanical valves, which are less likely to wear out, may also be used to replace a leaking mitral valve. However, when a mechanical valve is implanted, there is an increased risk of thromboembolism, and a patient is generally required to undergo extended anti-coagulant therapies.

One repair technique which has been shown to be effective in treating incompetence, particularly of the mitral and tricuspid valves, is annuloplasty, in which the effective size of the valve annulus is contracted by attaching a prosthetic annuloplasty ring to the endocardial surface of the heart around the valve annulus. The annuloplasty ring comprises an inner substrate of a metal such as stainless steel or titanium, or a flexible material such as silicone rubber or Dacron cordage, covered with a biocompatible fabric or cloth to allow the ring to be sutured to the heart tissue. The annuloplasty ring may be stiff or flexible, may be split or continuous, and may have a variety of shapes, including circular, D-shaped, C-shaped, or kidney-shaped. Examples are seen in U.S. Pat. Nos. 4,917,698, 5,061,277, 5,290,300, 5,350,420, 5,104,407, 5,064,431, 5,201,880, and 5,041,130, which are incorporated herein by reference.

During an annuloplasty procedure, an annuloplasty ring may be implanted on the mitral valve to cause the size of a stretched mitral valve 116 to be reduced to a relatively normal size. FIG. 3 is a schematic representation of a representative annuloplasty ring. An annuloplasty ring 304 is shaped approximately like the contour of a normal mitral valve. That is, annuloplasty ring 304 is shaped substantially like the letter "D." Typically, annuloplasty ring 304 may be formed from a rod or tube of biocompatible material, e.g., plastic, that has a DACRON mesh covering.

In order for annuloplasty ring 304 to be implanted, a surgeon surgically attaches annuloplasty ring 304 to the mitral valve on the atrial side of the mitral valve. Conventional methods for installing ring 304 require open-heart surgery which involve opening a patient's sternum and placing the patient on a heart bypass machine. As shown in FIG. 4, annuloplasty ring 304 is sewn to a posterior leaflet 318 and an anterior leaflet 320 of a top portion of mitral valve 316. In sewing annuloplasty ring 304 onto mitral valve 316, a surgeon generally alternately acquires a relatively large amount of tissue from mitral tissue, e.g. a one-eighth inch bite of tissue, using a needle and thread, followed by a smaller bite from annuloplasty ring 304. Once a thread has loosely coupled annuloplasty ring 304 to mitral valve tissue, annuloplasty ring 304 is slid onto mitral valve 316 such that tissue that was previously stretched out, e.g., due to an enlarged heart, is effectively pulled in using tension applied by annuloplasty ring 304 and the thread which binds annuloplasty ring 304 to the mitral valve tissue. As a result, a gap, such as gap 220 of FIG. 2b, between anterior leaflet 320 and posterior leaflet 318 may be substantially closed off. After the mitral valve is shaped by ring 304, the anterior and posterior leaflets 320, 318 will reform to create a new contact line and will enable mitral valve 318 to appear and to function as a normal mitral valve.

Once implanted, tissue generally grows over annuloplasty ring 304, and a line of contact between annuloplasty ring 304 and mitral valve 316 will essentially enable mitral valve 316 to appear and function as a normal mitral valve. Although a patient who receives annuloplasty ring 304 may be subjected to anti-coagulant therapies, the therapies are not extensive, as a patient is only subjected to the therapies for a matter of weeks, e.g., until tissue grows over annuloplasty ring 304.

In a modification of the above described annuloplasty approach, percutaneous annuloplasty devices and procedures have been developed, in which an annuloplasty device is positioned in the coronary sinus.

Annuloplasty rings may also be utilized in combination with other repair techniques such as resection, in which a portion of a valve leaflet is excised, the remaining portions of the leaflet are sewn back together, and a prosthetic annuloplasty ring is then attached to the valve annulus to maintain the contracted size of the valve. Other valve repair techniques in current use include commissurotomy (cutting the valve commissures to separate fused valve leaflets), shortening mitral or tricuspid valve chordae tendonae, reattachment of severed mitral or tricuspid valve chordae tendonae or papillary muscle tissue, and decalcification of the valve leaflets or annulus. Annuloplasty rings may be used in conjunction with any repair procedures where contracting or stabilizing the valve annulus might be desirable.

A second type surgical procedure which is generally effective in reducing mitral valve leakage involves placing a single edge-to-edge suture in the mitral valve. With reference to FIG. 5a, such a surgical procedure, e.g., an Alfieri stitch procedure or a bow-tie repair procedure, will be described. An edge-to-edge stitch 404 is used to stitch together an area at approximately the center of a gap 408 defined between an anterior leaflet 420 and a posterior leaflet 418 of a mitral valve 416. Once stitch 404 is in place, stitch 404 is pulled in to form a suture which holds anterior leaflet 420 against posterior leaflet 418, as shown. By reducing the size of gap 408, the amount of leakage through mitral valve 416 may be substantially reduced.

Another surgical procedure which reduces mitral valve leakage involves placing sutures along a mitral valve annulus around the posterior leaflet. A surgical procedure which places sutures along a mitral valve with be described with respect to FIG. 5b. Sutures 504 are formed along an annulus 540 of a mitral valve 516 around a posterior leaflet 518 of mitral valve 516, and may be formed as a double track, e.g., in two "rows," from a single strand of suture material. Sutures 504 are tied off at approximately a central point 506 of posterior leaflet 518. Pledgets 546 are often positioned under selected sutures 504, e.g., at central point 506, to prevent sutures 504 from tearing through annulus 540. When sutures 504 are tied off, annulus 540 may effectively be tightened to a desired size such that the size of a gap 508 between posterior leaflet 518 and an anterior leaflet 520 may be reduced.

Although efficient in restoring valve function, the above procedures and technologies do not address the decline in pump function of the heart muscle. In addition, the above described procedures are typically available only to patients with severely damaged valves.

There is, therefore, a continued need to develop new approaches to repairing cardiac, and particularly mitral valve, function, where of particular interest would be the development of a system for improving mitral valve function while at the same time restoring pump function of the heart. The present invention addresses this need.

RELEVANT LITERATURE

U.S. Pat. Nos. 5,243,976; 5,316,001; 5,376,112; 5,489,297; 5,554,177; 5,593,424; 5,709,695; 5,792,194; 5,824,066; 6,292,693; 6,539,261; 6,626,838; 6,643,546; 6,537,314; 6,565,603; 6,709,456; 6,718,985; and 6,723,038.

SUMMARY OF THE INVENTION

Methods and devices for modulating heart valve function are provided. In the subject methods, a heart valve is first in structurally modified. Blood flow through the structurally modified heart valve is then monitored, and the heart is paced in response to the monitored blood flow. Also provided are devices, systems and kits that find use in practicing the subject methods. The subject methods find use in a variety of applications.

DETAILED DESCRIPTION OF THE SPECIFIC EMBODIMENTS

Figure 1:
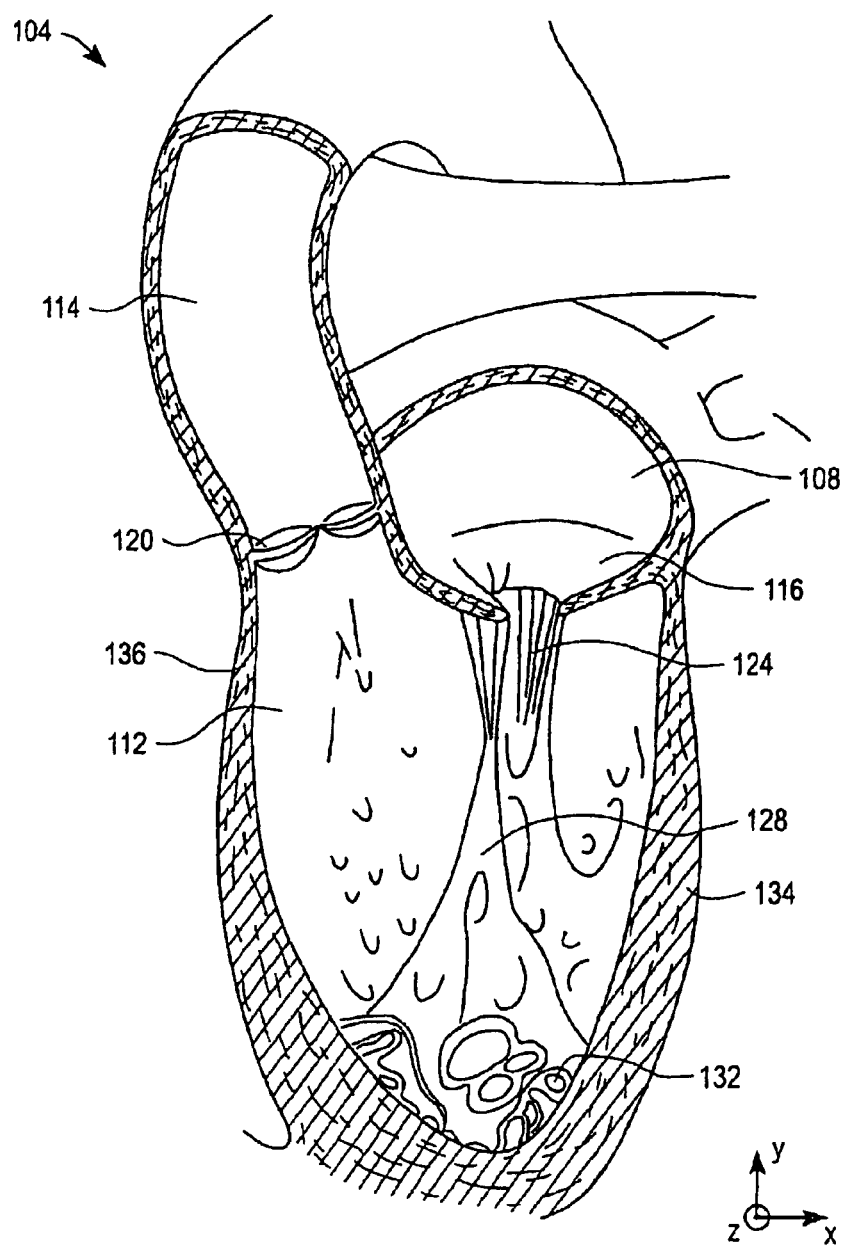
FIG. 1 is a cross-sectional front-view representation of the left side of a human heart.
Figure 2A:
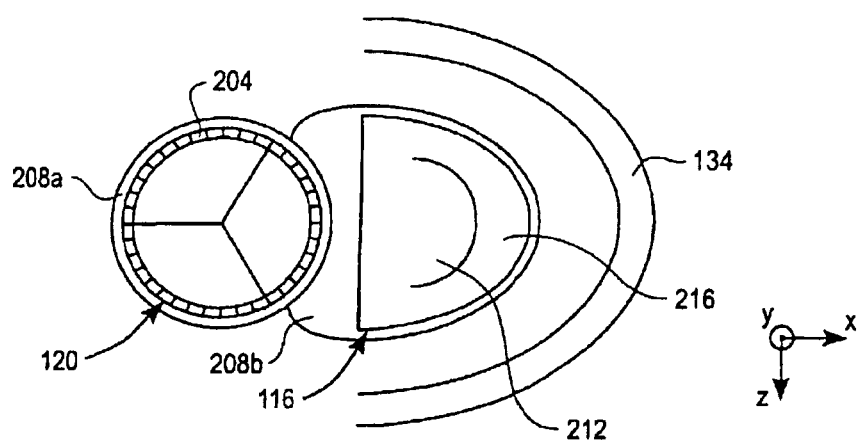
FIG. 2a is a cut-away top-view representation of the mitral valve and the aortic valve of FIG. 1.
Figure 2B:
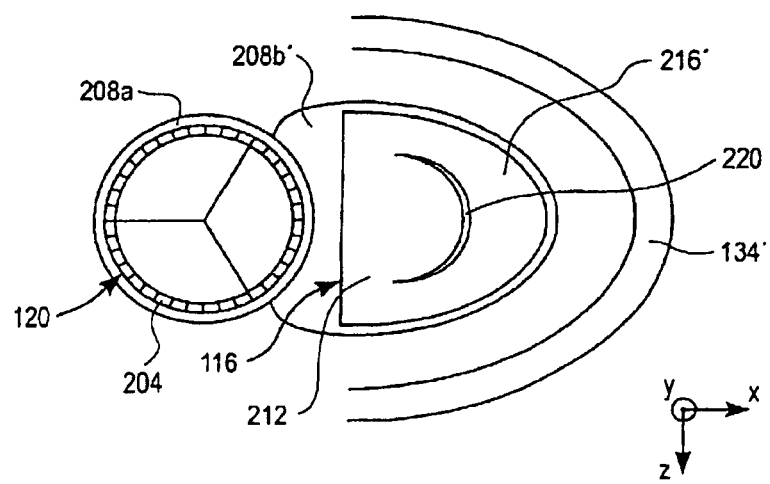
FIG. 2b is a cut-away representation of a stretched mitral valve and an aortic valve.
Figure 3:
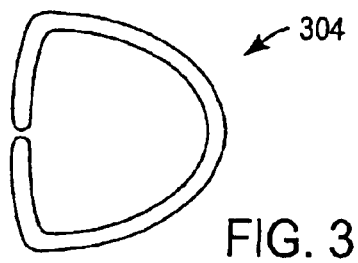
FIG. 3 is a representation of an annular ring that is suitable for use in performing a conventional annuloplasty procedure.
Figure 4:
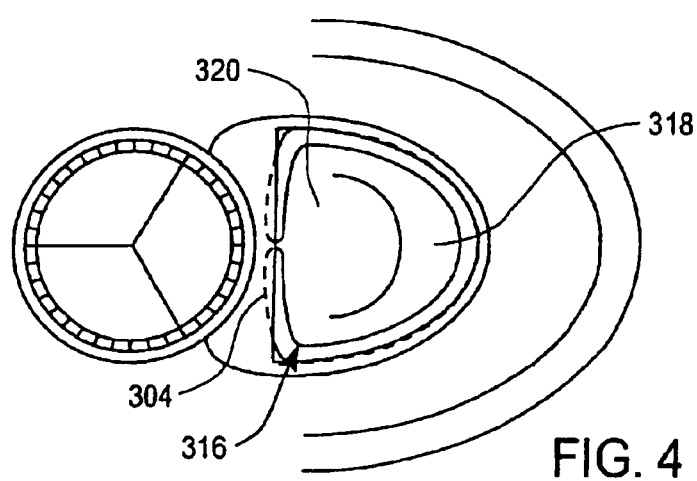
FIG. 4 is a representation of a mitral valve and an aortic valve after the annular ring of FIG. 3 has been implanted.
Figure 5A:
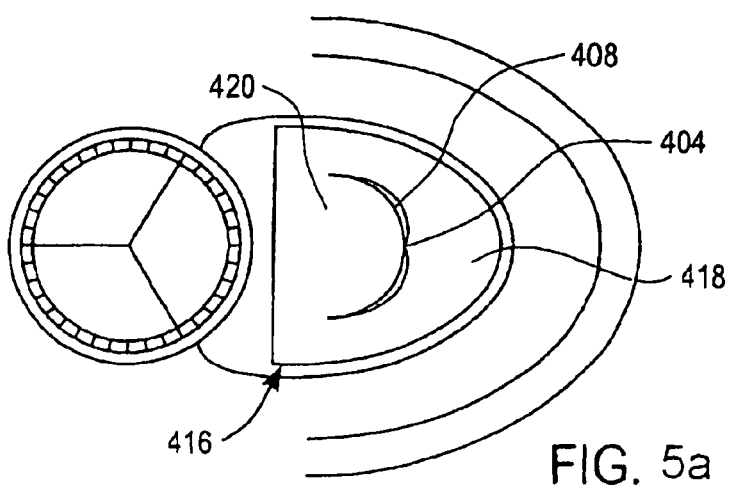
FIG. 5a is a representation of a mitral valve and an aortic valve after a single edge-to-edge suture has been applied to reduce mitral regurgitation.
Figure 5B:
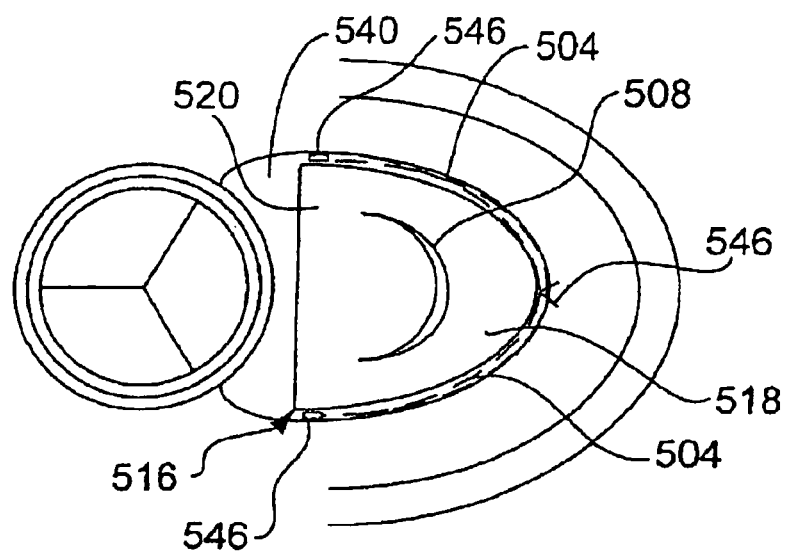
FIG. 5b is a representation of a mitral valve and an aortic valve after sutures along a mitral valve annulus have been applied to reduce mitral regurgitation.

Methods and devices for modulating heart valve function are provided. In the subject methods, a heart valve is first in structurally modified. Blood flow through the structurally modified heart valve is then monitored, and the heart is paced in response to the monitored blood flow. Also provided are devices, systems and kits that find use in practicing the subject methods. The subject methods find use in a variety of applications.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits; ranges excluding either or both of those included limits are also included in the invention.

Methods recited herein may be carried out in any order of the recited events which is logically possible, as well as the recited order of events.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described.

All publications mentioned herein are incorporated herein by reference to disclose and describe the methods and/or materials in connection with which the publications are cited.

It must be noted that as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

The publications discussed herein are provided solely for their disclosure prior to the filing date of the present application. Nothing herein is to be construed as an admission that the present invention is not entitled to antedate such publication by virtue of prior invention. Furthermore, the dates of publication provided may be different from the actual publication dates which may need to be independently confirmed.

As summarized above, the present invention provides methods and devices, as well as systems and kits, for modulating, and specifically improving, valve function in a subject. In further describing the subject invention, the subject methods are reviewed first in greater detail, followed by a more in-depth description of representative embodiments of systems and devices for practicing the subject methods, as well as a review of various representative applications in which the subject invention finds use. Finally, a review of representative kits according to the subject invention is provided.

Methods

As summarized above, the present invention provides methods of modulating the function of a target valve in a subject. The target valve is generally a cardiac valve (by which is meant that the valve is present in a heart), such as an aortic valve, mitral valve, tricuspid valve, etc. In many representative embodiments, the target valve is a mitral valve.

The subject in which the target valve is present in many embodiments of the present invention is a mammalian subject, i.e., is a "mammal" or "mammalian," where these terms are used broadly to describe organisms which are within the class mammalia, including the orders carnivore (e.g., dogs and cats), rodentia (e.g., mice, guinea pigs, and rats), lagomorpha (e.g. rabbits) and primates (e.g., humans, chimpanzees, and monkeys). In many embodiments, the hosts will be humans.

As indicated above, the subject methods are methods of modulating function of the target valve. By modulating is meant altering or changing the function of the target valve. In many representative embodiments, the modulating results in an improvement in the function of the target valve, e.g., in the form of reduced or even eliminated regurgitation. Where the modulation results in reduced regurgitation, the magnitude of the reduction may be at least about 5-fold, such as at least about 10-fold, including at least about 20-fold, as compared to a suitable control.

In practicing the subject methods, the target valve is first structurally altered. By structurally altered is meant that the target valve is surgically changed or modified in a manner that results in a change in the physical structure of the valve, e.g., in terms of diameter of the valve annulus, the physical orientation of two or more of the leaflets relative to each other, the physical structure of the leaflets and/or adjacent cardiac tissue, etc.

The target valve may be structurally altered using any convenient and desirable valve modification protocol, where a variety of suitable protocols and devices for practicing the same have been developed and may be employed. Representative valve alteration protocols of interest include, but are not limited to: annuloplasty procedures, in which the diameter of the target valve annulus is effectively reduced; procedures in which one or more sutures are placed on the valve leaflets in order to modify leaflet and therefore valve function; procedures in which tissue modifications, e.g., plications or folds, are produced proximal to the target valve to alter its function; and the like.

In many representative embodiments of the present invention, the structural modification or alteration of the target valve is achieved by an annuloplasty procedure. Any convenient annuloplasty procedure may be employed, where such procedures are reviewed generally in the Background section, above. The annuloplasty device and protocol may be open heart, e.g., where the device is positioned interstitially, or percutaneous, as is known in the art. Representative annuloplasty devices and protocols for their use are further described in U.S. Pat. Nos. 6,709,456; 6,565,603; 6,537,314; 5,824,066; 5,709,695; 5,593,424; the disclosures of which are herein incorporated by reference.

Following structural modification of the target valve, as described above, flow through the structurally modified target valve is monitored, where the obtained or observed flow data in this step is then employed as input in determining the desired pacing of the heart, as described in greater detail below. In this monitoring step of the subject methods, measurement of blood flow can be obtained through various blood flow measurement techniques. Representative blood flow measurement techniques of interest include, but are not limited to: sonic Doppler flow measurement techniques, e.g., continuous wave (CW) Doppler flow measurement and pulsed Doppler flow measurement; optical laser Doppler flow measurement; transit time flow measurement; thermal dilution flow measurement; and electromagnetic flow measurement.

As is known in the art, Doppler ultrasound imaging systems detect a Doppler shift in the frequency of a transmitted signal reflected from ultrasound reflectors, and display returns only from such reflectors. The magnitude of the Doppler shift corresponds to the velocity of the ultrasound reflectors, and the polarity of the Doppler shift corresponds to the direction of movement. Conventional Doppler images are thus able to provide an indication of both blood flow velocity and blood flow direction, thereby allowing arterial blood flow to be differentiated from venous blood flow.

Blood flow through the target valve may also be monitored by using electromagnetic flow techniques to estimate blood flow velocity. In one embodiment of this technique, at least first and second (i.e., two or more) electrodes are disposed across the target valve such that the blood flow is in a direction that is substantially orthogonal to a vector between the first and second electrodes. A permanent magnet or electromagnet is used to create a magnetic field through the blood vessel in a direction that is substantially orthogonal to both the direction of blood flow and the vector between the first and second electrodes. As a result, ionized particles within the blood flow are deflected toward one of the first and second electrodes, resulting in a voltage difference therebetween that is proportional to the blood flow velocity. In certain of these embodiments, a pulsed current may be employed to generate the magnetic field, as desired, e.g., to reduce the amount of heat generated by the electromagnet. In these representative embodiments, the duty cycle may range from about 0-100%, such as from about 0.01 to about 10%, including from about 1 to about 5%.

In yet other embodiments, blood flow through the target valve may be monitored using thermal dilution techniques to estimate blood flow. In one embodiment of this technique, a heater is used to pulsedly heat the blood, and the heated blood pulse is detected by a temperature sensor located at a known distance from the point of heating in the direction of the blood flow, where the temperature sensor may be at the valve or at a distance away from the valve, e.g., in the aorta. Volumetric blood flow is calculated from the time between the heating of the blood pulse and the detection of the blood pulse. Several heated blood pulses are typically introduced and detected to produce a more accurate blood flow estimate. In certain embodiments, a single thermistor may be used for both heating and detection. A heated thermistor is introduced into the blood vessel such that it is in thermal contact with the blood flow, and cooling of the thermistor is effected by the blood flow. Blood flow at a higher velocity cools the thermistor at a higher rate than blood flow at a lower velocity. The energy delivered to the thermistor to maintain the thermistor at a constant temperature is proportional to blood flow velocity. Alternatively, the thermistor can be heated to a known temperature, and the time required to cool the thermistor to a second, lower temperature will be inversely proportional to blood flow. In certain embodiments, the thermally sensed flow magnitude may be coupled with a direction component, which may be derived from the particular stage of the cardiac cycle at which the measurement is taken. As desired, suitable algorithms may be employed to achieve this coupling of magnitude of flow and direction.

In yet other embodiments, laser Doppler techniques may be employed to estimate blood flow. The blood flow is illuminated with a coherent monochromatic light source signal. A resulting backscattered Doppler-shifted light signal is received at an optical detector, and demodulated such as by mixing with the monochromatic light source signal. Blood flow velocity is estimated from a resulting basebanded Doppler-shifted frequency of the received light signal.

In certain representative embodiments, as described further below, the blood flow measuring device that is employed to monitor blood flow through the structurally altered target valve is part of an implantable device that was used in the target valve structural modification. In other words, the blood flow monitoring device is part of an implantable valvular structural modification device, such as an annuloplasty ring. In certain representative embodiments, the blood flow monitoring device is integrated with the implantable valve structure modification device.

In representative embodiments where the structural modification device is an implantable annuloplasty ring, such as an interstitial annuloplasty ring, the integrated flow monitoring element is an electromagnetic flow monitoring element. In these embodiments, a magnetic field is established by the device and detected variations in the established magnetic field are employed to determine flow velocity at a given time, as well as over or during a given temporal period. The magnetic field may be established using a number of different approaches, such as through of electromagnets; use of two or more permanent magnets, including rare earth magnets, such as neodymium; use of a material, such as a ferromagnetic material, within the magnetic field inducing components, to increase the magnitude of the magnetic field; and the like. In certain embodiments, the established magnetic field may be modulated by a carrier frequency, such that the voltage measured by the electrodes would also be modulated by a carrier frequency, such as 500 Hz, thus making it possible to create a flow-dependent voltage signal at a frequency range outside of the range of frequencies generated by pacemakers and/or the myocardium. In certain embodiments, a voltage sensing unit associated with the two or more electrodes.

In representative embodiments of annuloplasty devices having integrated electromagnetic flow sensor elements, the implantable annuloplasty device may have a partial ring shape within the plane of the valve and a wire may be looped around the device in a manner sufficient to produce the desired magnetic field across the plane of the valve. In certain embodiments, the apparatus may be one that positions two or more magnets arranged around the circumference of the diameter of the valve, e.g., such as 2 or more, 3 or more, 4 or more, 5 or more, 10 or more, 20 or more, etc. In embodiments having a sufficient number of different magnets, the direction of the magnetic can be changed within the plane of the vale activating a current producing field into the vale, and also activating a subset of magnets pointing out of the vale.

As summarized above, in practicing the subject methods, data obtained by monitoring the flow through the valve, e.g., by using a separate flow meter or a flow meter integrated with an implantable valve structure modulation (such as annuplasty) device, is used to at least partially modulate electrical stimulation (also referred to herein as pacing) of the heart. In other words, obtained flow meter data or information is employed to influence, e.g., determine or set, etc., how the heart is paced, e.g., from an implanted cardiac stimulation or pacing device.

In such embodiments, the implanted cardiac pacing device is one that is implanted in a manner sufficient to modulate function of the structurally altered target valve. Any convenient pacing device and protocol may be employed, where protocols and implantable devices for use therein for modulating valve function via electrical stimulation or pacing are known in the art. The pacing device employed may having a single pacing site or multiple pacing sites. Representative such protocols and devices include those described in U.S. Pat. Nos. 6,643,546; 6,292,693; 5,554,177; the disclosures of which are herein incorporated by reference. In representative embodiments, the pacing is myocardial pacing. In representative embodiments, the pacing is epicardial pacing.

A feature of the manner in which data from the flow meter is employed to modulate pacing is that the modulation is automatic, by which is meant that the modulation occurs without a human operator first evaluating the flow data and then directly or manually modulating the pacing element. Instead, a processing means in operational communication with the flow meter and the pacing element automatically modulates the activity of the pacing element based on input received from the flow meter, e.g., by selecting an appropriate pacing protocol or routine based on predetermined flow parameters. Accordingly, in representative embodiments, the processing means may match or pair the observed flow data with a set of different predetermined flow parameters, and then select a pacing routine which is paired with the best matched flow parameter of the set.

As indicated above, practice of the subject methods results in a modulation of function of the target valve. By modulation of function is meant a change or alteration in the manner which the target valve mechanically operates, e.g., in controlling fluid flow across between regions separated by the valve. In many embodiments, the modulation is an improvement in the mechanical functioning of the valve, such that the valve functions in a manner that more approximates the functioning of a "normal" valve, which is an analogous valve from a subject in normal health.

Systems

Also provided are systems for use in practicing the subject methods, where the systems include at least: a target valve structural alteration element, a flow monitoring element, a pacing element and a processing element that provides for the operational communication between the flow meter and pacing elements, as described above. In certain embodiments, one or more of the various elements are integrated into a single structure, e.g., such as an integrated annuplasty and electromagnetic flow measurement device as described above. Representative embodiments of each of the above elements of the subject systems have been provided above.

In addition, the subject systems may further include one or more additional components which are useful and/or needed for successful operation of the system. For example, the system may further include a power supply element, e.g., a battery. The system may further include a receiving element for receiving data and/or power remotely, such as a telemetric receiving element for receiving power and/or instructions from a remote location, e.g., outside of the body, radiofrequency receiving element, optical receiving element, etc.

Computer-Related Embodiments

The invention also provides a variety of computer-related embodiments. Specifically, the invention provides programming for a processing means that can control a system as described above. The programming may be coded onto computer-readable medium, and the programming and the processor may be part of a computer based system.

In representative embodiments, the above methods are coded onto a computer-readable medium in the form of "programming", where the term "computer readable medium" as used herein refers to any storage or transmission medium that participates in providing instructions and/or data to a computer for execution and/or processing. Examples of storage media include floppy disks, magnetic tape, CD-ROM, a hard disk drive, a ROM or integrated circuit, a magneto-optical disk, or a computer readable card such as a PCMCIA card and the like, whether or not such devices are internal or external to the computer. A file containing information may be "stored" on computer readable medium, where "storing" means recording information such that it is accessible and retrievable at a later date by a computer.

With respect to computer readable media, "permanent memory" refers to memory that is permanent. Permanent memory is not erased by termination of the electrical supply to a computer or processor. Computer hard-drive ROM (i.e. ROM not used as virtual memory), CD-ROM, floppy disk and DVD are all examples of permanent memory. Random Access Memory (RAM) is an example of non-permanent memory. A file in permanent memory may be editable and re-writable.

A "computer-based system" refers to the hardware means, software means, and data storage means used to analyze the information of the present invention.

The minimum hardware of the computer-based systems of the present invention comprises a central processing unit (CPU), input means, output means, and data storage means. A skilled artisan can readily appreciate that any one of the currently available computer-based system are suitable for use in the present invention. The data storage means may comprise any manufacture comprising a recording of the present information as described above, or a memory access means that can access such a manufacture.

To "record" data, programming or other information on a computer readable medium refers to a process for storing information, using any such methods as known in the art. Any convenient data storage structure may be chosen, based on the means used to access the stored information. A variety of data processor programs and formats can be used for storage, e.g. word processing text file, database format, etc.

A "processor" references any hardware and/or software combination which will perform the functions required of it. For example, any processor herein may be a programmable digital microprocessor such as available in the form of a electronic controller, mainframe, server or personal computer (desktop or portable). Where the processor is programmable, suitable programming can be communicated from a remote location to the processor, or previously saved in a computer program product (such as a portable or fixed computer readable storage medium, whether magnetic, optical or solid state device based). For example, a magnetic medium or optical disk may carry the programming, and can be read by a suitable reader communicating with each processor at its corresponding station.

Utility

The subject invention finds use in valve function modulation applications, and particular in methods of improving valve function, e.g., in the treatment of a given disease or condition. By treatment is meant at least an amelioration of the symptoms associated with the disease condition afflicting the host, where amelioration is used in a broad sense to refer to at least a reduction in the magnitude of a parameter, e.g. symptom, associated with the pathological condition being treated, such as size of tumor, rate of growth of tumor, spread of tumor, etc. As such, treatment also includes situations where the pathological condition, or at least symptoms associated therewith, are completely inhibited, e.g., prevented from happening, or stopped, e.g. terminated, such that the host no longer suffers from the pathological condition, or at least the symptoms that characterize the pathological condition.

In certain representative embodiments where the target valve is a mitral valve and the condition or disease being treated is mitral valve regurgitation or leakage, practice of the subject methods can be evaluated or measured by a reduction in the levels of symptoms associated with heart failure, as classified by the New York Heart Association (NYHA) functional classification system. In this classification system, the levels range from a Class 1 level that is associated with an asymptomatic patient who has substantially no physical limitations to a Class 4 level which is associated with a patient who is unable to carry out any physical activity without discomfort, and has symptoms of cardiac insufficiency even at rest. In general, correcting for mitral valve leakage or regurgitation via practice of the subject invention may be successful in allowing the NYHA classification grade of a patient to be reduced. For instance, a patient with a Class 4 classification may have his classification reduced to Class 3 and, hence, be relatively comfortable at rest. In yet other embodiments, a patient with a Class 3 classification may have his classification reduced to Class 2, or a Class 2 patient may have his classification reduced to a Class 1, thereby resulting in improvement of the patient condition.

Kits

Also provided are kits for use in practicing the subject methods, where the kits typically include one or more of the above devices, and/or components of the subject systems, as described above. As such, a representative kit may include a device, such as implantable annuloplasty device, as described above. The kit may further include other components which may find use in practicing the subject methods.

In addition to above—mentioned components, the subject kits typically further include instructions for using the components of the kit to practice the subject methods. The instructions for practicing the subject methods are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging) etc. In other embodiments, the instructions are present as an electronic storage data file present on a suitable computer readable storage medium, e.g. CD-ROM, diskette, etc. In yet other embodiments, the actual instructions are not present in the kit, but means for obtaining the instructions from a remote source, e.g. via the Internet, are provided. An example of this embodiment is a kit that includes a web address where the instructions can be viewed and/or from which the instructions can be downloaded. As with the instructions, this means for obtaining the instructions is recorded on a suitable substrate.

The following examples are offered by way of illustration, and not by way of limitation.

EXPERIMENTAL

I. Example of System with Interstitial Annuloplasty Device

Figure 6:
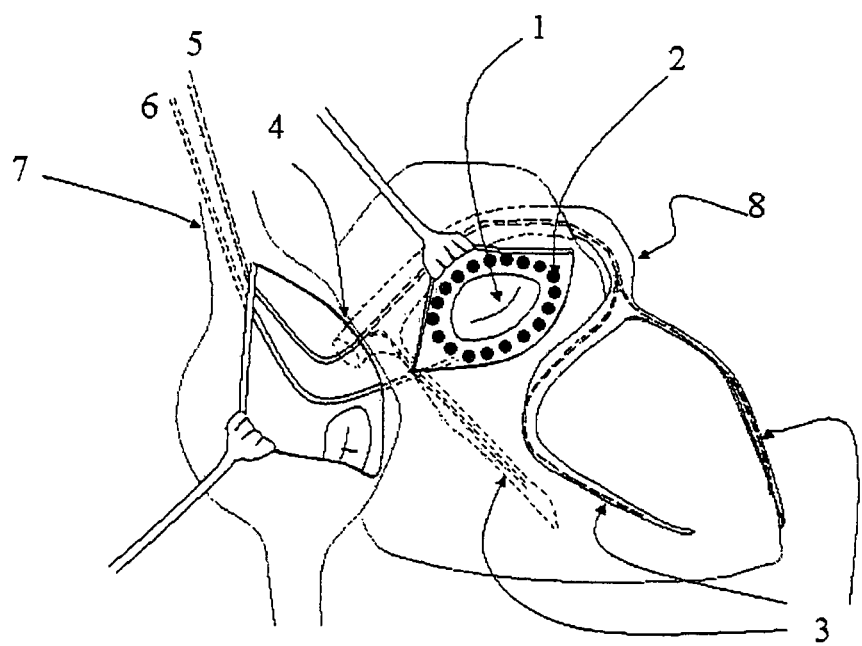
FIG. 6 provides a representative view of a system according to the subject invention as positioned to treat mitral valve regurgitation, as described in greater detail in the Experimental Section, below.
Figure 7:
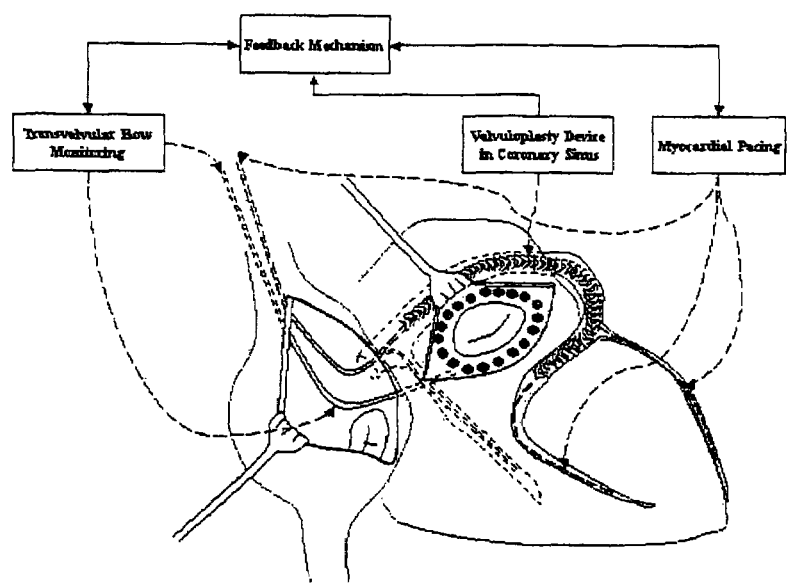
FIG. 7 provides a diagram of the operational relationship of the various components of the system as controlled by the central processing unit.

FIG. 6 provides a view of a mitral valve treated according to the subject invention with an interstitial annuloplasty device. In the system represented in FIG. 7, a peri-valvular implant is inserted around the insufficient valve to bring the valvular orifice to a desired size and shape, thereby restoring the valvular function to an optimal level. The valvular implant is equipped with technology to sense transvalvular flow and detect valvular leakage. Additionally, epicardial electrodes are placed in association with weakened and/or arrhythmic segments of the heart. Both, the valvular implant and the epicardial electrodes are connected to a central processing unit which coordinates the degree of transvalvular flow with subsequent pacing of individualized segments of the myocardium. Specifically, FIG. 7 shows the anterior view of the heart. In FIG. 7, a malfunctioning mitral valve (1) is surgically treated with an interstitial implant (2), which restores the size and shape of the valve. Addition, the interstitial perivalvular implant (2) is equipped with sensing technology to monitory transvalvular flow, and detect leakage of the valve. Information from the perivalvular sensors is transmitted through connection wires (6) which could perforate anatomical heart barriers such as the atrial septum (4) in order to reach desired anatomical paths such as the superior cava vein, en route to a remotely implanted pace maker (central processing unit), (not depicted). The transvalvular flow monitor (2) receives energy and transmits information through connection wires (6). Additionally, pacing electrodes (3) for stimulation of myocardial segments are inserted into close proximity to the surface of the heart, e.g. in the coronary venous system (8). The pacing electrodes (3) receive energy and coordination from a remotely implanted pace maker (central processing unit) through wire connections (5). FIG. 8 depicts the operational relationship of the system components.

As evidenced by the above, the present invention provides methods and systems for improving valve malfunction, which methods and systems are characterized by coupling mechanical repair of heart valve with electrical stimulation of the associated heart segments to restore pump function. In representative embodiments, an interstitial implant is inserted around an insufficient mitral valve to bring the valvular orifice to a desired size and shape, thereby restoring the valvular function to an optimal level. The interstitial valvular implant is equipped with technology to sense transvalvular flow and detect valvular leakage. Additionally, epicardial electrodes are placed in association with weakened and/or arrhythmic segments of the heart. Both the interstitial valvular implant and the epicardial electrodes are connected to a central processing unit which coordinates the degree of transvalvular flow with subsequent pacing of individualized segments of the myocardium, thereby providing for improvement in valve and heart function. Accordingly, the present invention represents a significant contribution to the art.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. A method of modulating the function of a cardiac valve in a heart and using a cardiac pacing protocol or routine for cardiac pacing, said method comprising:
    (a) structurally altering said cardiac valve for modulating a function thereof;
    (b) monitoring blood flow velocity by an implanted blood flow velocity measuring device through said structurally altered cardiac valve;
    (c) pacing said heart by an implanted cardiac pacing device in response to said monitoring to modulate function of said cardiac valve; and
    (d) receiving blood flow velocity information from said implanted blood flow velocity measuring device by an implanted processing element in operational communication with said blood flow velocity measuring device and said cardiac pacing device, said implanted processing element transmitting data relating to a cardiac pacing protocol or routine to said implanted cardiac pacing device by selecting the cardiac pacing protocol or routine based on predetermined blood flow velocity information, wherein said implanted processing element is operative without operator evaluation of the blood flow velocity information to automatically modulate the activity of said implantable cardiac pacing device using the selected cardiac pacing protocol or routine.

2. The method according to claim 1, wherein said modulating results in an improvement in said cardiac valve function.

3. The method according to claim 2, wherein said cardiac valve is a mitral valve.

4. The method according to claim 3, wherein said structurally altering comprises performing an annuloplasty procedure on said mitral valve.

5. The method according to claim 4, wherein said annuloplasty procedure employs an implantable annuloplasty device.

6. The method according to claim 5, wherein said annuloplasty device is an interstitial device.

7. The method according to claim 1, wherein said blood flow velocity measuring device is a sonic device.

8. The method according to claim 1, wherein said blood flow velocity measuring device is an optical device.

9. The method according to claim 1, wherein said blood flow velocity measuring device is a thermal device.

10. The method according to claim 1, wherein said blood flow velocity measuring device is an electromagnetic device.

11. The method according to claim 1, wherein said blood flow velocity measuring device is in operational communication with an implanted cardiac pacing device.

12. The method according to claim 1, wherein said blood flow velocity measuring device is integrated with an implantable annuloplasty device employed in said structural altering step.

13. The method according to claim 12, wherein said blood flow velocity measuring device is an electromagnetic device.

14. The method according to claim 1, wherein said pacing is epicardial pacing.

15. The method according to claim 1, wherein said method is a method of improving function of a mitral valve, wherein said method comprises structurally altering said mitral valve by employing an interstitial annuloplasty device; wherein said monitoring comprises employing an electromagnetic blood flow velocity measurement element integrated with said interstitial annuloplasty device, wherein said blood flow velocity measuring device is in operational communication with an implanted cardiac pacing device that paces said heart according to step (c).

16. A system for modulating the function of a cardiac valve in a heart and using a cardiac pacing protocol or routine for cardiac pacing, said system comprising:
    (a) an implantable device for structurally altering a cardiac valve for modulating a function thereof;
    (b) an implantable blood flow velocity measuring device for monitoring blood flow velocity through a cardiac valve;
    (c) an implantable cardiac pacing device in operational communication with said blood flow velocity measuring device;
    (d) a storage medium for storing a plurality of cardiac pacing protocols or routines, and
    (e) an implantable processing element in operational communication with said blood flow velocity measuring device and said cardiac pacing device, said implantable processing element receiving blood flow velocity information from said blood flow velocity measuring device and transmitting information relating to a cardiac pacing protocol or routine to said cardiac pacing device; wherein said implantable processing element is operative without operator evaluation of the blood flow velocity information to automatically modulate the activity of said cardiac pacing device based on the cardiac pacing protocol or routing;
    wherein the implantable processing element selects at least one of the cardiac pacing protocols or routines from the storage medium based on predetermined blood flow velocity information.

17. The system according to claim 16, wherein said cardiac valve is a mitral valve.

18. The system according to claim 16, wherein said implantable device is an annuloplasty device.

19. The system according to claim 1, wherein said annuloplasty device is a surgically implanted device.

20. The system according to claim 19, wherein said annuloplasty device is an interstitial device.

21. The system according to claim 16, wherein said blood flow velocity measuring device is a sonic device.

22. The system according to claim 16, wherein said blood flow velocity measuring device is an optical device.

23. The system according to claim 16, wherein said blood flow velocity measuring device is a thermal device.

24. The system according to claim 16, wherein said blood flow velocity measuring device is an electromagnetic device.

25. The system according to claim 16, wherein said blood flow velocity measuring device is integrated with said implantable device for structurally altering a cardiac valve.

26. The system according to claim 25, wherein said implantable device is an annuloplasty device.

27. The system according to claim 26, wherein said annuloplasty device is a surgically implanted device.

28. The system according to claim 27, wherein said annuloplasty device is an interstitial device.

29. The system according to claim 28, wherein said blood flow velocity measuring device is an electromagnetic device.

30. An implantable system for structurally altering a cardiac valve and providing cardiac pacing protocol or routine information, wherein said implantable system comprises:
   an implantable device for structurally altering a cardiac valve for modulating a function thereof;
   an integrated blood flow velocity measuring device, said device operational for providing cardiac pacing data in the form of a cardiac pacing protocol or routine to an implantable cardiac pacing device for pacing a heart by electrical stimulation in response to measured blood flow velocity information by said blood flow velocity measuring device;
   a storage medium for storing a plurality of cardiac pacing protocol or routines; and
   an implantable processing element in operational communication with said blood flow velocity measuring device, said storage medium and said cardiac pacing device, said implantable processing element receiving information from said blood flow velocity measuring device and transmitting to said cardiac pacing device a cardiac pacing protocol or routine based on predetermined blood flow velocity information;
   wherein said implantable processing element is operative without operator evaluation of the blood flow velocity information to automatically modulate the activity of said cardiac pacing device by selecting the cardiac pacing protocol or routine based on predetermined blood flow velocity information.

31. The system according to claim 30, wherein said cardiac valve is a mitral valve.

32. The system according to claim 31, wherein said implantable device is an annuloplasty device.

33. The system according to claim 32, wherein said annuloplasty device is a surgically implanted device.

34. The system according to claim 33, wherein said annuloplasty device is an interstitial device.

35. The system according to claim 30, wherein said blood flow velocity measuring device is a sonic device.

36. The system according to claim 30, wherein said blood flow velocity measuring device is an optical device.

37. The system according to claim 30, wherein said blood flow velocity measuring device is a thermal device.

38. The system according to claim 30, wherein said blood flow velocity measuring device is an electromagnetic device.

39. The system according to claim 30, further including a cardiac pacing device in operational communication with said blood flow velocity measurement device.

40. A kit for modulating the function of a cardiac valve in a heart and using a cardiac pacing protocol or routine, said kit comprising:
   (a) an implantable device for structurally altering a cardiac valve for modulating a function thereof;
   (b) an implantable blood flow velocity measuring device for monitoring blood flow through a cardiac valve;
   (c) an implantable cardiac pacing device for providing electrical stimulation to a heart in operative communication with said blood flow velocity measuring device, wherein said electrical pacing stimulation is in the form of a cardiac pacing protocol or routine;
   (d) a storage medium for storing a plurality of cardiac pacing protocols or routines; and
   (e) an implantable processing element in operational communication with said blood flow velocity measuring device, said storage medium and said cardiac pacing device, said implantable processing element receiving information from said blood flow velocity measuring device and transmitting to said cardiac pacing device a cardiac pacing protocol or routine based on predetermined blood flow velocity information;
   wherein said implantable processing element is operative without operator evaluation of the blood flow velocity information to automatically modulate the activity of said cardiac pacing device.

41. The kit according to claim 40, wherein said cardiac valve is a mitral valve.

42. The kit according to claim 41, wherein said implantable device is an annuloplasty device.

43. The kit according to claim 42, wherein said annuloplasty device is a surgically implanted device.

44. The kit according to claim 43, wherein said annuloplasty device is an interstitial device.

45. The kit according to claim 40, wherein said blood flow velocity measuring device is a sonic device.

46. The kit according to claim 40, wherein said blood flow velocity measuring device is an optical device.

47. The kit according to claim 40, wherein said blood flow velocity measuring device is a thermal device.

48. The kit according to claim 40, wherein said blood flow velocity measuring device is an electromagnetic device.

49. The kit according to claim 40, wherein said blood flow velocity measuring device is integrated with said implantable device for structurally altering a cardiac valve.

50. The kit according to claim 49, wherein said implantable device is an annuloplasty device.

51. The kit according to claim 50, wherein said annuloplasty device is a surgically implanted device.

52. The kit according to claim 51, wherein said annuloplasty device is an interstitial device.

53. The kit according to claim 50, wherein said blood flow velocity measuring device is an electromagnetic device.

54. The kit according to claim 40, wherein said cardiac pacing device is an epicardial pacing device.

55. The kit according to claim 40, wherein said kit further comprises instructions for using said kit.

* * * * *